United States Patent [19]

Kokubu

[11] Patent Number: 4,457,913
[45] Date of Patent: Jul. 3, 1984

[54] COMPLETE ANTIGEN DRUG AND A PROCESS FOR PRODUCING IT FOR NONSPECIFIC ALLERGIC DISEASE THERAPY

[76] Inventor: Tadao Kokubu, 2-3, Ooi 2-chome, Shinagawa-ku, Tokyo, Japan

[21] Appl. No.: 350,550

[22] Filed: Feb. 19, 1982

[30] Foreign Application Priority Data

Mar. 4, 1981 [JP] Japan .................................. 56-29941

[51] Int. Cl.$^3$ ...................... A61K 37/02; A61K 39/00
[52] U.S. Cl. ...................................... 424/88; 424/177
[58] Field of Search .................................. 424/177, 88

[56] References Cited

U.S. PATENT DOCUMENTS 4,235,771 11/1980 Adams ........................ 260/112.5 R

FOREIGN PATENT DOCUMENTS 2677 7/1979 European Pat. Off. .
14984 9/1980 European Pat. Off. .
15810 9/1980 European Pat. Off. .
2070619 9/1981 United Kingdom .

Primary Examiner—Delbert R. Phillips
Assistant Examiner—F. T. Moezie
Attorney, Agent, or Firm—Jordan and Hamburg

[57] ABSTRACT

An antigen drug or a process of producing it available for the oral, the percutaneous and the permucous membrane immunotherapies with autoimmunization equilibrium induced in feeling of cold, what is called "HIE-SHO" in Japanese, contracting nonspecific allergic diseases caused from auto-antigen-antibody reaction by atypical antibody. The antigen drug is available in the liquid type and the ointment type which are effective to the percutaneous and the permucous membrane immune therapies of non-specific allergic diseases. The antigen drug is made from urea of normal and healthy person.

3 Claims, 1 Drawing Figure

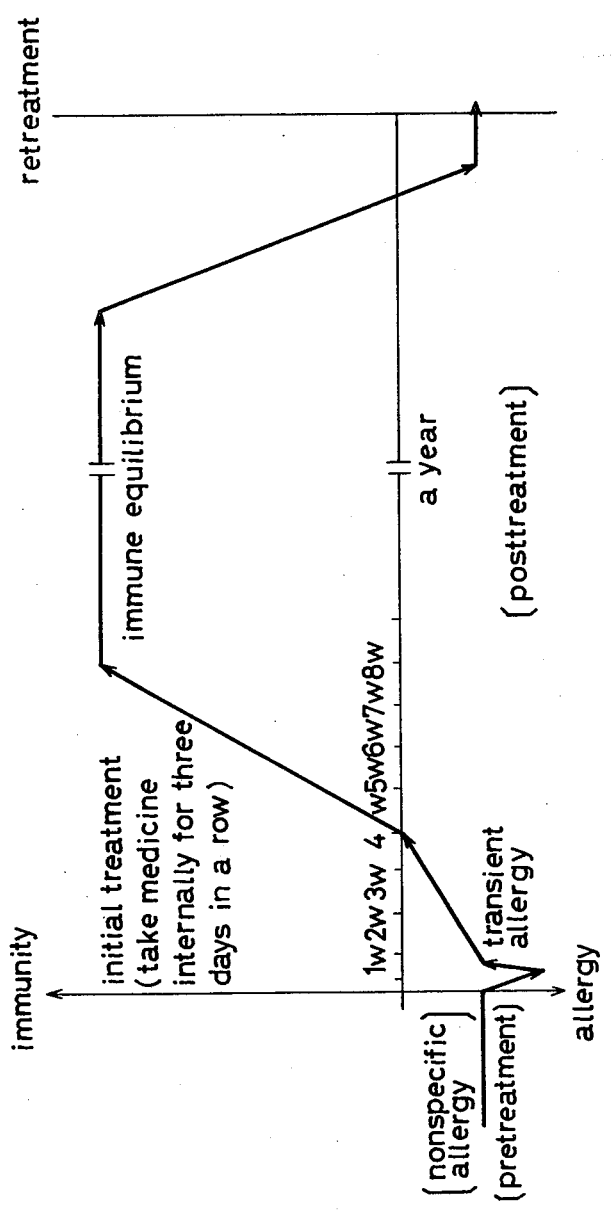

COMPLETE ANTIGEN DRUG AND A PROCESS FOR PRODUCING IT FOR NONSPECIFIC ALLERGIC DISEASE THERAPY

This invention relates to an antigen drug and a process for producing it and making it available for oral, percutaneous and permucous membrane immunotherapies through autoimmunization for the syndrome identical with "the feeling of cold" in English (so called "HIESHO" in Japanese) i.e., contracting nonspecific allergic diseases caused from auto-antigen-antibody reaction.

Until recently such nonspecific allergic diseases have never been differentiated exactly from specific allergic diseases, although the latter criteria for the latter of genesis and mechanism have been studied thoroughly from ancient times.

In this paper the term "nonspecific allergy" is used often without discrimination.

In my opinion, nonspecific allergic diseases are defined as follows:

Their onset is due to antigen (not exactly exogen antigen, but exogen antigen modified in the body, for example, modified immunoglobulin G) or essentially antigen produced in the body and antibody or antigen-antibody complexes in co-operation.

From this point of view nonspecific allergic diseases resemble autoimmune diseases or both are essentially identical.

Thus autoimmune diseases and nonspecific allergic diseases occur at any time without any contact with exogen antigens but due to endogenous antigen-antibody reaction.

These mechanisms are triggered anywhere in tissues so that if it occurred mainly in the abdomen, especially the pelvis, we call it "HIESHO" or "the feeling of cold" and if it occurs otherwise we call it the equivalent of "HIESHO."

Nonspecific allergic diseases have a high rate of incidence and a characteristic of causing chronic relapses, especially with women.

These characteristics and symptoms have been confirmed from substantial study results.

(1) Nonspecific allergic diseases based on a hereditary allergic constitution have their onset when the autonomic nervous system, the internal secretion system and the metabolism receive exogenous or endogenous stimuli, and develop various symptoms.

(2) Nonspecific allergic diseases based on auto-antigen-antibody reaction are among various allergic diseases.

(3) Nonspecific allergic diseases are chronic recurrent ones and occur from babies to the old, and especially in women.

Nonspecific allergic diseases have crucial influences on menstruation, pregnancy and erotogenic function and thus disturb family life.

(4) These nonspecific allergic diseases are classified into the abdomen-, the small pelvis-, the airway-, the skin-, the bone joint- and other types. There are many cases in which the abdomen and the small pelvis types are accompanied with blood circulation troubles, and these types are referred to as causing "the feeling of cold" in a narrow meaning. And other types are referred to as "allergic equivalent".

(5) Nonspecific allergic diseases have various combinations of types, but never lead to death by themselves.

(6) We can classify these diseases as having short term and long term duration. The former has a duration of a few days and the latter has a duration of a few years. The above terms respectively consist of the prodrome, the paroxysm, the disappearance and the panse.

(7) Frequent paroxysms of these nonspecific allergic diseases leave a physical stigma.

Experimental Background (1) The distinctive erythrocyte agglutination response was recognized when serum of a post partum woman was added to auto-erythrocyte pretreated with tannic acid (diluted 400 fold in distilled water) and also with auto-placental tissue extract of a pregnant woman suffering from nonspecific allergic disorders essentially as well as severe pregnancy intoxication.

(2) The $\gamma$-globulin fraction gained by treating multivalued human urine with ammonium sulfate and purified sensitize rabbits to create antihuman urine $\gamma$-globulin rabbit antiserum. In accordance with P. L. Mollison who modified the original Coombs method, Coombs direct method was carried out. As a result, positive Coombs response in patients, when the patients had paroxysms, was found at high rate compared with normal persons.

(In this specification, multivalued human urine is defined as "urine which is collected from a plurality of healthy persons.")

(3) It has turned out that antihuman urine $\gamma$-globulin rabbit antiserum shows a cross immune response in various ways to human serum, secretion, excretion, organ, and tissue extract.

From the above description, I can not help concluding that atypical antibodies exist broadly within the human body, and have a close relation to the true cause of nonspecific allergic diseases.

From ancient times, oral and local therapies with human urine have been generally spread as private therapy with the pharmaceutical action unknown. And these days, sugar which is produced by eliminating protein from human urine is percutaneously, as infection, used in desensitization of asthma and other relative allergic diseases with remarkable success.

It was not conventionally assumed that protein derived from blood, except for small quantities of ablumin and Bence Jones protein, was excreted in normal human urine. More recently, as analytical methods have made great progress, it has been found that some kinds of globulin other than albumin, mucoprotein, protein polysaccharide and the like are excreted in human urine, and, in addition, that degraded transferrin, macroglobulin, lipoprotein and so forth exist in normal human urine.

The total amount of protein in normal early-morning human urine ranges from 3 mg/dl to 100 mg/dl of which the amount of $\gamma$-globulin is about 70%. Most of these excreted proteins are of the protein polysaccharide type.

As for oral immunity, 40 years ago, the Frenchman Besredka studied local immunity against intestinal tract infection and gave pills of heat denatured sterile vaccine. But his trial failed because a large amount of blood antibodies were produced in comparison with the extent of local immunity. Then the creation of local immunity was attempted by giving a mixture of B.C.G. vaccine with milk to babies for intestinal tuberculosis. But B.C.G. reaches the lymph nodes of the mesenteric wall through the intestinal tract and grows slowly and produces a little bit of local immunity but at the same time, produces a large amount of antibodies systemically. It is well known that Sabin established the antipolio immunity method in which an infant takes poliovirus vaccine internally and acquires antipolio immunity. The mechanism is explained as follows;

In the intestinal wall, weak-toxic poliovirus, S-immuno γ-globulin A, J-chain and the like produce an immune complex. This immune complex develops into a barrier. Then the resulting barrier immune complex prevents virus from entering into the intestinal tract and further prevents viremia from developing. Generally, S-immunoglobulin A complex plays the role of the barrier against hetero- or iso-protein passing through villi and prevents hetero- or iso-protein from entering into the intestinal tract. Therefore, when the amount of S-immunoglobulin A complex is reduced for some reason, the general and autoimmune mechanisms are broken down. As a result, bovine serum albumin antibody increases in amount in body fluid after drinking cow's milk, but generally hetero-protein is transformed into aminoacid in intestinal wall and assimilated by liver enzyme action, then reconstructed into autoprotein after being conveyed to cell.

Except for a specific case, there is no instance in which diet-hetero-protein disturbs the immune mechanism. On the contrary, in the case where iso- or au-tourea-protein is taken internally, it is clear that they have an influence on the process for producing immunity. There is a response similar to the delayed type cellular immunity as already described above. If iso-protein is transformed into aminoacid on the intestinal wall, and causes destruction of the antigen critical group, it does not provoke an immune response and therefore the above description does not hold.

In the cases of killed vaccine and B.C.G. vaccine established by Besredka in order to produce local immunity in the intestinal tract, and the vaccine established by Sabin, the action of the vaccine on the lymph nodes of the intestinal wall stimulates cellular immunity and then systemic antibody production results. With respect to nonspecific antigens such as iso- or auto-urea-protein, I cannot help considering that, by entirely the same way as above, systemic immunity is produced.

Therefore, one of the objects of the present invention is to provide an antigen drug for therapy of nonspecific allergic diseases, as "feel of cold", by induction of auto-immunity.

Another object of the invention is to provide an antigen drug for nonspecific allergic diseases therapy, which consists of protein polysaccharide abstracted from normal human urine as its effective ingredient.

Another object of the invention is to provide an antigen drug and a process for producing its effective agent for oral immune therapy by which autoimmunity to nonspecific allergic diseases is induced or the establishment of delayed type cellular immunity is promoted.

A further object of the invention is to provide an antigen drug suitable for oral immune therapy of nonspecific allergic diseases which drug patients can take internally with ease and a process for producing said drug.

A further object of the invention is to provide a powdered antigen drug suitable for oral immune therapy of nonspecific allergic diseases.

A still further object of the invention is to provide an antigen drug effective for percutaneous or permucous membrane immune therapy of nonspecific allergic diseases and a process for producing said drug.

A still further object of the invention is to provide an antigen drug effective to percutaneous or permucous membrane immune therapy of nonspecific allergic diseases, which in liquid or ointment form is easily possible to spray on or to apply directly to skin and mucous membrane and a process for producing said drug.

A still further object of the invention is to provide an antigen drug for nonspecific allergic diseases therapy, which doesn't have any toxicity as medicament nor oncogenicity.

Other objects and features of this invention will become apparent from the specification and claims when embodiments of this invention are considered in connection with the drawings, in which:

FIG. 1 depicts an average pattern for the transition of immune recovery illustrating a case where an antigen drug of this invention is applied for oral immune therapy.

This invention uses normal urine of healthy men as a starting material. Necessary quantities of sodium hydroxide and calcium chloride anhydride are added to normal urine and then stirred. Then the resulting white precipitate absorbs molecules of protein polysaccharide in the urine. Supernatant liquid is separated from the precipitate as much as possible. Successively, after adding sterile refined water to the precipitate, the necessary number of times of the centrifugal irrigation washing is done to refine the white precipitate. The calcium protein polysaccharide compound resulting from dehydrating the wet precipitate is triturated to be suitable for oral therapy. Or, after dialysing normal urine as starting material with current water and distilled water for necessary period, protein polysaccharide is corrected into a certain concentration by the artificial-wind-dehydration, and successively is diluted into a certain concentration with bases to be suitable for percutaneous and permucous membrane therapy. This antigen drug for nonspecific allergic diseases therapy consists of protein polysaccharide as the effective component.

An embodiment of the process for producing the oral antigen drug for nonspecific allergic diseases therapy in this invention is described in detail as follows.

Urine obtained from healthy persons (age 18–35, preferably male) in early morning, which is proved protein negative by the sulfosalicylic acid method, is collected and then is dialyzed with water in a sterile tube for 48 hours. The dialyzed urine is preserved by freezing until the quantity amounts to 5 liters in all. Tests using microscopy and various kinds of culture are carried out in a part of the urine to ascertain that there is no bacteria, microorganism, true fungi, and so forth present. Additionally, for caution's sake, the urine is sterilized by pressure filtration in an ultrafilter having meshes of $0.45\mu$. The resulting urine is the starting material. This multivalued urine which is collected from healthy persons shows a weak-acidity of pH6.5.

1N. sodium hydroxide solution, pH9–10 is added to the urine. Calcium chloride anhydride is added to the urine at a rate of 10w/v% and stirred, resulting in the formation of a white precipitate. The amount of molecules of protein polysaccharide absorbed by and precipitated with the white precipitate reaches to 40–50% of the amount of urine.

Then, after the supernatant liquid is separated as much as possible without causing turbulence of the precipitate, the precipitate is divided into sterile centrifugal precipitation tubes and then centrifuged and washed at 2000 rpm for fifteen minutes after adding sterile water. The number of fifteen times of this repeated centrifuging and washing operation removes the urine coloration and makes the precipitate white to the naked eye.

Successively, this wet precipitate is enclosed with sterile filter paper and then dried with drying-air under blast (adjusted to 30° C.). As a result, a calcium protein polysaccharide compound is produced. In the last stage, this compound is triturated in a sterile mortar to be suitable for use as the oral antigen drug of this invention for nonspecific allergic disease therapy.

The characteristics of the oral antigen drug as above produced and its content of protein polysaccharide are as follows.

The oral antigen drug of this invention is a light-yellow-white, tasteless and odorless powder and the yield is 4.95 g from the amount of 5 l urine. The oral antigen drug is not soluble in water, alkali liquid, organic solvent, but is dissolved in acid liquid of around pH2. Accordingly, to examine the quantities and properties of the protein polysaccharide in calcium protein polysaccharide, the oral antigen drug is dissolved in acid and enclosed in a sterile tube. Then, this acid liquid is dialyzed with distilled water for 24 hours. The liquid becomes neutral and calcium cloride is eliminated.

With the protein quantity method of T. C. A. Ponceau using trichloroacetic acid and pigment, the content of protein in the original urine is 8.2 mg/dl and the content of protein in the calcium protein polysaccharide precipitate supernatant liquid is 2.04 mg/dl. Therefore, in the calcium protein polysaccharide, about 75% of the protein quantity in the urine is captured.

The total protein quantity of dried calcium protein polysaccharide comes to 308 mg in quantitative conversion by the T. C. A. Ponceau method, and the protein content therein comes to 62.6 mg per one gram of powder. In the oral therapy, dried calcium protein polysaccharide powder is diluted ten times with lactose. A dose of 0.5 g is internally administered once a day so that administration quantity of protein for a dose is 3.13 mg.

The components and content of the oral antigen drug are as follows;
(a) Sugar: (Carbol-sulfuric acid method) 55 mg/dl.
(b) Content of stiffened lipid, organic compounds (as urine, uric acid, creatine, etc.) and minerals except calcium are respectively shown in the table below. Here the reagent is a solution of pH6.7 in which 0.1 g calcium protein polysaccharide is dissolved in 10 cc hydrogen chloride of pH2 and then dialyzed for twenty four hours. (unit mg/dl).

| main organic compounds other than lipid | urine nitrogen (N) 0.5 | uric acid 0 | creatine 0.3 | bilirubin 0 | sugar 2 |
|---|---|---|---|---|---|
| content of lipid | β-lipoprotein 4 | cholesterol 2 | neutral fat 2 | phosphatide 11 | free fatty acid 0.01 |
| content of main minerals | Na 12 meg/l | K 0.6 meg/l | Cl 4 meg/l | Ca 5.2 meg/l | P 2.17 meg/dl | Mg 2.17 meg/l |

As the for immunological properties of protein polysaccharide in urine, the protein in urine responds to antihuman serum protein (and its fraction) and anti-rabbit (or -goat) serum. Antihuman urine γ-globulin rabbit antisera respond widely to protein antigen in secretion, exudate, organ, and tissue extracts of human serum. Common immune bodies, which widely exist in human body and protein polysaccharide, are excreted into urine from serum through the kidney.

The oral immune mechanism of calcium protein polysaccharide in this invention is now stated. The solution of calcium protein polysaccharide in gastric juice liberates protein polysaccharide, since calcium protein polysaccharide dissolves in acid solution (pH2–3.5). Then, protein polysaccharide dissolved in alkaline intestinal juice is absorbed by villi. Within the intestinal wall, immune globulins (the domain of γ-globulin) in protein polysaccharide are captured by local macrophage and leukocyte and therefore antigen determination radical, residual bases in immune globulin (the domain of γ-globulin) are exposed. This antigen recognition is transmitted to cells of the lymph system in lymph nodules and then blastization of lymphocyte is triggered. Blastized lymphocytes start to propagate with fission cause a chain reaction repeatedly in themselves by stimulation of biological product similar to lympha kine. As a result, the antibody produced by blast cells correct breaking of immunity in body fluids and keeps immune equilibrium for a long time in cooperation with cellular and body fluids immunities.

The oral immune therapy will now be described.

[I] Internal use application

A dose of 0.5 g calcium protein polysaccharide powder (containing 3.13 mg protein), which is 10 times as weak as its original through dilution with lactose or glucose, is internally taken once a day on an empty stomach. In the initial immunity, a dose is internally taken at the same time for three days in a row. These three doses for three days are called 1Kur. The medicine is taken with a little bit of water in the same way as general powder medicines are taken, but it is better to take this medicine with acidulous liquid of a pickled plum, diluted hydrochloric acid limonaze and so forth.

[II] Target of therapy

Careful examination of nonspecific allergic patients is carried out to try to remove mingled symptoms caused from organic diseases. Further, a 5 mg tablet of pledonisolon, which is a kind of adreno-cortical hormone drug is taken twice a day for a week to ascertain disappearance of symptoms-complexes. Immune therapy is done on the basis that symptoms are due to mainly functional disorders. The following report is based on physical examinations, selecting 25 patients (male 5, female 20, age 16–65) at random among 102 patients who received treatment.

[III] Sumary of complaints

Patients had been suffering from the following complaints or their combination as stated in TABLE I for two to thirteen years.

TABLE I

| Order | Complaint | % |
|---|---|---|
| 1 | abdominal inflation and pain | 92 |
| 2 | low back pain | 72 |
| 3 | coldness of limbs, abdomen and waist | 68 |
| 4 | anorexia, nausea, emesis | 64 |
| 5 | vertigo, heavy-headedness, orthostatic syncope, cephalalgia | 64 |
| 6 | constipation | 56 |
| 7 | loose passage, diarrhea | 52 |
| 8 | general fatigue | 48 |
| 9 | weight loss | 44 |
| 10 | leukorrhea disorder | 40 |
| 11 | dysmenorrhea | 35 |
| 12 | shoulder, back inflation and pain | 32 |
| 13 | lethargy, sleeplessness | 28 |
| 14 | joint pain, myalgia, neuralgia | 28 |
| 15 | vulvar pruritus | 15 |
| 16 | hemorrhoids | 15 |

In addition to complaints as in TABLE I, eczema, common cold, asthma, urticaria, sterility, purpura and others were variously found.

[IV] Result of treatment and standard of judgment

1. Two months before and after the treatment, the following criteria are comparably examined and then the effect is judged generally.
   (1) Alleviation or disappearance of main symptom and complaint, improvement of existing problems in light of consultation, and weight increase.
   (2) Improvement of objective index The cellular and humoral responses known in immunology were practiced in accordance with necessity.

The above criteria, by the usual immuno-cellular and -humoral examinations, were determined as follows:

Materials:

Early morning autourine was taken as antigen. Autoblood was taken simultaneously, partially for autoserum separation and partially as heparin blood for cellular elements separation, amounting to about 20 ml in total.

Experiments:

1. L.M.T.

Here autourine was diluted with physiologic NaCl solution from 1000 to 10 billion fold in 6 steps. Separated autoleucocytes were incubated with autourine dilution series at 37° C. for 1 hour.

Thus pretreated leucocytes were quantitatively poured into agarose wells while in the center well leucocytes pretreated with P.B.S. negative solution was poured.

After 24 hours incubation at 37° C., agarose schale was taken out and examined on leucocytes migration area.

Results: In nonspecific allergic diseases leucocytes migration was extremely depressed due to mingled lymphokines.

2. P.H.A.

In this experiment autolymphocytes blasting ratio was compared between 10 million fold diluted autourine, P.H.A. (T cell mitogen), 20 thousands fold diluted and P.B.S. negative contrast after 24 hours incubation at 37° C.

Results: If immunity was kept $u>p>(-)$, immune activity is raised. If immunity was kept $p>u>(-)$, autoallergy is raised. u: urea, p: P.H.A.

3. T.B.D. cell count.

Performed as usual.

Results: In allergic stadium T cell % decrease under 70% while B cell % increase above 20%. In immune phase T cell % above 80% while B cell % under 12%. C cell behavior was not constant.

4.

Total lymphocytes number decrease in allergic stadium, while in immune phase it increases.

5.

Immuno $\gamma$-globulin quantity shows no remarkable changes in any case.

However, in a judgment of the present status and transition of nonspecific allergy which is basically considered as nonspecific autoimmune disease, it is difficult to conclude that some responses always reflect immune status faithfully. Accordingly, the four tests described below are practiced as a necessary indication.

(1) Intracutaneous response using refined urine protein polysaccharide (containing 10 mg/dl).

(2) Action of protein polysaccharide in refined autourine to autoperipheral lymphocytes (with other kinds of leukocytes mixed) causes their blasting, agglutination, and fission (mitogenic function like some vegetable mitogens for example P.H.A.). Hence, it is inspected opto-microscopically and then compared in a multiple dilution row of protein polysaccharide in refined autourine.

(3) As described above, auto-antibody is absorbed on autoerythrocyte membrane. Agent of refined protein polysaccharide in autourine to autoerythrocyte pretreated with tannic acid, causes erythrocytes to agglutinate. Polyvalency of auto-antibody is judged by comparing multiple dilution of autourine in row; (direct Coombs).

(4) Refined autourine protein polysaccharide produces clot to auto blood plasma under existence of tannic acid solution (400 fold diluted with distilled water.) There are individual differences in relation between dilution of protein polysaccharide in urea and clot time (first step, second step and completion). These differences are co-relative to the symptoms of a patient. In the nonspecific allergic diseases group screening especially No. 4 examination reflex well recent, conditions of diseases and autoimmunity disharmony, and further (2)–(4) shows positive or negative co-relation in the same case.

2. Result

The cure rate is shown in the following table on the basis of the above judgments and criteria.

(1) Cure Table

| results | judgements and criteria | among 5 men | % | among 20 women | % | total |
|---|---|---|---|---|---|---|
| very good | main symptom: disappearance of most of problems and weight increasing index: greatly improved | 4 | 16 | 17 | 68 | 84% |
| better | main symptom: getting better of most of problems and weight | 1 | 4 | 1 | 4 | 8% |

-continued

| results | judgements and criteria | among 5 men | % | among 20 women | % | total |
|---|---|---|---|---|---|---|
| unchanged | increasing index: improved main symptom: unchangeability of problem, unchangeability of weight | 0 | 0 | 1 | 4 | 4% |
| worse | index: unchanged main symptom: problems getting worse weight decreasing index: worse | 0 | 0 | 1 | 4 | 4% |

As shown in the above table, the very good and better cases in results amounted to 92% of all cases.

(2) An unchangeable case

A woman of 45 years had been suffering from non-specific allergic diseases for twenty years and this was accompanied with depression from ten years ago. The result is shown in the column of the unchanged in the above cure table. This case was judged unchangeable; however, it was found that the condition of the patient got better during the past four months. But the patient took medicine internally after one and half years (booster oral immunization).

(3) A worse case

A woman of 43 years had been suffering from non-specific allergic diseases for ten years and this was accompanied with rheumatoid arthritis for a few years. Two months after she took protein polysaccharide medicine internally, she had repeatedly a slight fever and reddening, swelling and pain of joints with weight decreasing. The index was worse. This case was in typical allergic disorder. The further treatment was stopped at once.

[V] Transient irritation symptom (allergy symptom) after the internal therapy. Transition to and continuation of immune equilibrium (judgment of the time limit and necessity of re-treatment)

1. It is considered that this therapy method activates systemical cellular immunity (and following humoral immunity) through the intestinal tract. Therefore this method is characterized by appearance of transient allergy symptom within the range of 24–48 hours after contact of protein polysaccharide with lymph nodes in the mesenteric wall.

2.

(1) The situation in which no symptom was complained of. 16% (4 cases).
(2) The situation in which condition and complaint were transiently worse. 52% (13 cases).
(3) The situation in which a hitherto unexperienced symptom appeared. 32% (8 cases).

| Table of items in (3) | | | | | |
|---|---|---|---|---|---|
| Symptom | No. | % | Symptom | No. | % |
| urticaria | 2 | 25 | asthma | 2 | 25 |
| arthritis, arthralgia | 1 | 12.5 | diarrhea | 1 | 12.5 |
| rhinitis allergic | 1 | 12.5 | purpura | 1 | 12.5 |

3. The duration of allergic phase from the first day the drug was internally taken

| Duration | No. | % | Duration | No. | % |
|---|---|---|---|---|---|
| 0 day | 4 | 16 | 6–7 days | 2 | 8 |
| 1 day | 1 | 4 | 8–15 days | 1 | 4 |
| 2 days | 4 | 16 | 16 days–1 month | 1 | 4 |
| 3 days | 7 | 28 | 1 month– | 1 | 4 |
| 4–5 days | 4 | 16 | | | |

That is, after protein polysaccharide was given, 84% out of the total cases had a transient allergic phase. 88% out of the cases, including non-symptom cases, experienced transient allergic symptoms within 7 days after the protein polysaccharide was internally taken.

4. Transition of immune recovery

The transition period in which the immunizing mechanism is accelerated, where patient falls into a transient allergic condition and reaches equilibrium before long, shows extreme individual differences. According to age, sex, the degree of nonspecific allergic diseases, location of the main symptom, presence or absence of accompanying diseases, the duration of the oral immunity is modified.

As the average pattern of this transition is shown in FIG. 1, the duration for the equilibrium is about two months.

5. Condition posterior to completion of equilibrium (1) The improvement and absence of subjective symptoms, that is, especially great improvement of various symptoms (feeling of cold, slight fever, heavy-headedness, sleepiness, irritation, shoulder discomfort, abdominal and low back pain etc.) due to autoimmune disturbances and interruption in peripheral blood circulation, improvement of objective problems, normalization of stomach function, improvement of metabolism and so forth equally result in weight increasing and recovery of a feeling of health.

(2) There may be unavoidable cases, however, where recovered autoimmunity is disturbed transiently owing to daily and seasonable factors after equilibrium is attained. However, this unbalanced condition is by far more stable than that of pre-treatment and becomes normal in a shorter time. As for the remarkable symptom, anti-inflammation faculty increases. Further it seems to have prophylactic force against malignant tumor eruption, but can not assure the fact owing to lack of remote results.

6. Additional immunity and prognosis

The duration of equilibrium is from one to a few years but is strongly subject to the individual differences and some conditions stated in the above transition of immune recovery. The timing for additional immunity is determined by the reduction of indices and the reappearance of symptoms and complaints. As for additional immunity, protein polysaccharide doses are determined according to said criteria, whether the medicines are taken three times, or the medicines are taken twice and a booster is given a week later, or only a booster is taken once.

Rational repetition of this therapeutic method settles homeostasis of immunity forever without any necessity for re-treatment.

7. Side effects (bad reaction)

(1) Over-sensitization

In the initial immunization, calcium protein polysaccharide diluted ten times in the amount of 0.5 g (containing protein of 3.13 mg) a day is internally taken 3 times for 3 days in a row. If the medicine is internally taken 7 times for 7 days in a row, the patient would develop a crucial allergic condition without exception. The patient would not die but would suffer for a few years. The same case occurs when too much of calcium protein polysaccharide or protein is internally taken for three days in a row or when retreatment is begun by misjudging the timing of the end of immunity equilibrium.

(2) Remote influences of calcium protein polysaccharide

Urine calcium protein polysaccharide need not be considered for its undesirable effect upon oncogenesis and genetic consequences etc. because of its biological origin.

Embodiments of the method for producing percutaneous and permucous membrane drugs for therapy of nonspecific allergic equivalents are now presented in detail.

Multivalued human urine, as starting material, is treated in the same way as in the production of said oral antigen drug. It is dialyzed with current water for 24 hours and then distilled water for 24 hours. Successively, the resulting multivalued human urine is dried artificially under air blast and then the protein concentration is corrected to 1000 mg/dl, and the result is mingled with base of a saline solution, water, alcohol, ointment, etc. at the rate of 100 g/100 mg of protein polysaccharide. These antigen drugs are given through a percutaneous and a permucous membrane in chronic allergic diseases of skin; for example, chronic eczema. They show extremely good effect in 24-48 hours after use. But, a few days later recidive relapse of these diseases is seen, so that these drugs need to be used repeatedly. Probably, it is assumed that absorbed protein polysaccharide shows cellular immunity effect under interaction between cells after contact with subcutaneous lymph nodes but doesn't show local immunity for a long time because the subcutaneous lymph organ is a low level one as the immune organ and the resulting immune compound is diluted and dispersed by the circulatory system.

Here, the local use on a percutaneous and a permucous membrane is explained.

(1) Application to skin chronic eczema

If protein polysaccharide is applied to exudate eczema once a day, dampness is stopped after 24-28 hours and pruriginous effect disappears after drying. The progress is extremely favorable.

(2) Application to seborrheic eczema of the head

As in (1), the itchiness is stopped and the resultant dandruff falls off.

(3) In urticaria, skin herpes, extremely good effect is shown.

(4) In cases (1) and (2), however, if the local use is stopped for a few days, the symptoms appeared again. This point is basically different from the results observed for oral immunity and most important. Accordingly, in chronic eczema, the local use is repeated at least every three days and in addition the oral therapy of calcium protein polysaccharide is used simultaneously.

As described above, various kinds of clinical experiments were carried out on the basis of the immune mechanism of antigen-antibody reaction. As a result, it has become clear that the antigen drug of this invention is extremely effective against nonspecific allergic diseases for the treatment of which the conventional drugs do not provide comparable results.

The oral, the percutaneous and the permucous membrane antigen drugs of this invention for therapy of nonspecific allergies are especially effective against a feeling of cold from which nonspecific allergy patients suffer and against which effective treatment methods have not previously been provided. The production method of this invention makes mass production possible and this invention will have a huge influence on the medical industry.

What is claimed is:

1. An antigen drug for therapy of nonspecific allergic diseases comprising a protein polysaccharide free from any adjuvants as its effective ingredient, said polysaccharide being obtained by a process comprising collecting normal human urine from healthy persons, preferably men, of age 10-35, testing said urine in accordance with the sulfosalicylic acid method to prove that it is protein negative, dialyzing the protein negative urine with water in a sterile tube, adding sodium hydroxide solution having pH 9-10 to the dialyzed urine to which calcium chlride anhydride is also added and stirred so as to cause a white precipitate to form, allowing particles of said precipitate to absorb the protein polysaccharide in the urine, separating the supernatant fluid as soon as possible, refining the white precipitate by centrifugal washing with water, repeating this washing a plurality of times, and triturating the resulting calcium protein polysaccharide compound after sterile drying thereof.

2. The drug of claim 1 wherein, in said process, the dialyzed urine is preserved by freezing, a sample of said urine is examined for existence of bacteria, microorganism and fungi and, if indicated by the examination, the urine is sterilized by a pressure filtration process.

3. The drug of claim 1 wherein, in said process, the quantity of protein polysaccharide absorbed by said white precipitate reaches to about 40-5-% of the urine quantity.

* * * * *